United States Patent [19]

Oyama et al.

[11] Patent Number: 4,487,717
[45] Date of Patent: Dec. 11, 1984

[54] PROCESS FOR RECOVERING A DIPEPTIDE DERIVATIVE

[75] Inventors: Kiyotaka Oyama, Shin-nanyo; Shigeaki Irino, Tokuyama; Norio Hagi, Shin-nanyo, all of Japan

[73] Assignees: Toyo Soda Manufacturing Co., Ltd., Shin-nanyo; Sagami Chemical Research Center, Tokyo, both of Japan

[21] Appl. No.: 415,912

[22] Filed: Sep. 8, 1982

[30] Foreign Application Priority Data

Sep. 21, 1981 [JP] Japan .................. 56-147974
Sep. 22, 1981 [JP] Japan .................. 56-148754
Sep. 22, 1981 [JP] Japan .................. 56-148755
Sep. 22, 1981 [JP] Japan .................. 56-148756

[51] Int. Cl.³ .......................... C07C 103/52
[52] U.S. Cl. .......................... 260/112.5 R
[58] Field of Search ................ 260/112.5 R; 424/177

[56] References Cited

U.S. PATENT DOCUMENTS

| | | | |
|---|---|---|---|
| 3,678,026 | 7/1972 | Ariyoshi et al. | 260/112.5 R |
| 3,808,190 | 4/1974 | Dahlmans et al. | 260/112.5 R |
| 3,833,553 | 9/1974 | Ariyoshi et al. | 260/112.5 R |
| 4,119,493 | 10/1978 | Isowa et al. | 260/112.5 R |
| 4,165,311 | 8/1979 | Isowa et al. | 260/112.5 R |

FOREIGN PATENT DOCUMENTS 1309605 3/1973 United Kingdom .

*Primary Examiner*—Delbert R. Phillips
*Assistant Examiner*—F. Moezie
*Attorney, Agent, or Firm*—Oblon, Fisher, Spivak, McClelland & Maier

[57] ABSTRACT

A process for recovering a dipeptide derivative comprises admixing an aqueous mixture of a solid dipeptide ester derivative of the formula

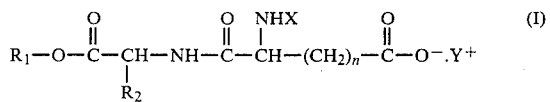

wherein $R_1$ is a lower alkyl group, $R_2$ is a side chain group of an amino acid, n is 1 or 2, X is a benzyloxycarbonyl group which can have a nuclear substituent and Y is a hydrogen ion or an ammonium derivative ion of the formula

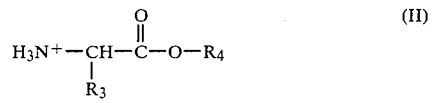

wherein $R_3$ is a side chain group of an amino acid and $R_4$ is a lower alkyl group with an organic solvent capable of forming a binary phase system with water; said solvent being present in an amount effective to obtain the transfer of said peptide in the form of a solid from the aqueous phase to the organic solvent phase, settling the resulting admixture to form (1) an organic solvent phase containing in a solid state a substantial amount of dipeptide derivative of the formula

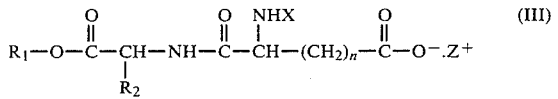

wherein $R_1$, $R_2$, n and X are as defined above and Z is a hydrogen ion or an ammonium derivative ion of the formula

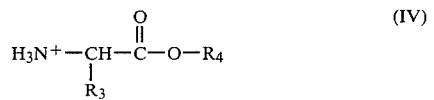

wherein $R_3$ and $R_4$ are as defined above, and
(2) an aqueous phase, separating the organic solvent phase from the aqueous phase, and recovering the dipeptide derivative from the organic solvent phase.

34 Claims, No Drawings

PROCESS FOR RECOVERING A DIPEPTIDE DERIVATIVE

FIELD OF THE INVENTION

The present invention relates to a process for recovering a dipeptide derivative. More particularly, it relates to a process for recovering a dipeptide derivative from an aqueous suspension thereof with use of an organic solvent.

DESCRIPTION OF THE PRIOR ART

An addition compound of a dipeptide ester such as an N-benzyloxycarbonyl-α-L-aspartyl-L-phenylalanine lower alkyl ester with an amino acid such as a phenylalanine lower alkyl ester or a valine lower alkyl ester, is useful as an intermediate for an α-L-aspartyl-L-phenylalanine lower alkyl ester which is a sweetener or as an intermediate for optical resolution of an amino acid racemic modification.

Such an addition compound is obtainable, for instance, by reacting an N-protected aminodicarboxylic acid with an amino acid ester in an aqueous medium in the presence of a protease (U.S. Pat. No. 4,165,311 and U.S. Pat. No. 4,256,836) or by reacting a dipeptide ester with an amino acid ester in a solvent such as water (Japanese Unexamined Patent Publication No. 19234/80 and No. 73644/80). In these reactions, the addition compound precipitates as a solid component in the aqueous medium. Further, a substantial amount of still active protease remains, as dissolved, in the aqueous medium in the former case. Accordingly, it is very important to efficiently recover the addition compound as well as the protease from the aqueous medium.

In the above mentioned conventional methods, the recovery of the addition compound is conducted by filtration, while no recovery of the protease is carried out.

It is also known to add an organic solvent capable of forming a binary phase system with water to the reaction mixture whereby the addition compound is dissolved and extracted in the solvent and can be separated in a form of a uniform solution in the organic solvent (U.S. Pat. No. 4,212,946). In order to efficiently carry out the extraction, the organic solvent should be capable of not only forming a binary phase system but also providing a great solubility for the addition compound. However, there are only a limited number of organic solvents which satisfy these requirements. Typical ones are esters such as ethyl acetate or alkyl halides such as 1,2-dichloroethane. However, esters have a problem that they are susceptible to hydrolysis, while alkyl halides are recently suspected to be a carcinogen and it should be avoided to use them for the treatment of the addition compound which is used as a starting material for foods.

On the other hand, if the organic solvent is less effective to dissolve the addition compound, it will be necessary to use it in a greater amounts, this being an economical disadvantage.

SUMMARY OF THE INVENTION

The present inventors have conducted an extensive research to overcome the above mentioned difficulties and to develop an industrially advantageous process for separating the addition compound, and as a result, have unexpectedly found that in a binary phase system comprising an aqueous phase and an organic solvent phase, crystals of the addition compound are taken into the organic solvent phase in the solid state and can thereby be effectively separated from the aqueous phase containing the unreacted material and protease. Thus, the present invention has been accomplished.

Namely, the present invention provides a process for recovering a dipeptide derivative which comprises admixing an organic solvent capable of forming a binary phase system with water with an aqueous mixture containing as a solid component a dipeptide ester derivative of the formula

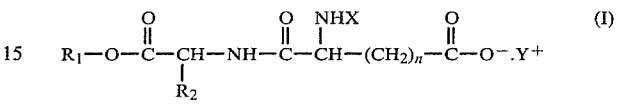

wherein $R_1$ is a lower alkyl group, $R_2$ is a side chain group of an amino acid, n is 1 or 2, X is a benzyloxycarbonyl group which can have a nuclear substituent and Y is a hydrogen ion or an ammonium derivative ion of the formula

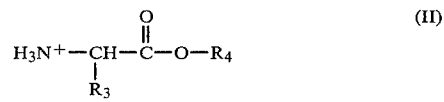

wherein $R_3$ is a side chain group of an amino acid and $R_4$ is a lower alkyl group, settling the resulting admixture to form (1) an organic solvent phase containing in a solid state a substantial amount of dipeptide derivative of the formula

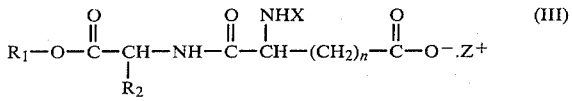

wherein $R_1$, $R_2$, n and X are as defined above and Z is a hydrogen ion or an ammonium derivative ion of the formula

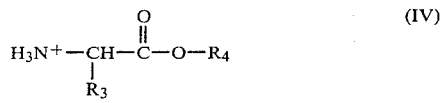

wherein $R_3$ and $R_4$ are as defined above, and (2) an aqueous phase, separating the organic solvent phase from the aqueous phase, and recovering the dipeptide derivative from the organic solvent phase.

DETAILED DESCRIPTION OF THE PREFERRED EMBODIMENTS

In the above formulas, each of $R_1$ and $R_4$ is a lower alkyl group such as a methyl group, an ethyl group, a propyl group or a butyl group, and each of $R_2$ and $R_3$ is a side chain group of an amino acid such as a methyl group, an isopropyl group, an isobutyl group, an isoamyl group, a benzyl group or a p-hydroxybenzyl group. Particularly preferred as $R_2$ is a benzyl group. X may be a benzyloxycarbonyl group which may have a substituent on its nucleus, such as a benzyloxycarbonyl group or a p-methoxybenzyloxycarbonyl group.

The aqueous mixture containing the addition compound of the general formula (I) in a solid state may be obtained by reacting an amino acid ester of the formula $$R_1-O-\overset{\overset{O}{\|}}{C}-\underset{\underset{R_2}{|}}{CH}-NH_2 \qquad (V)$$

wherein $R_1$ and $R_2$ are as defined above, with an N-protected aminodicarboxylic acid of the formula $$HO-\overset{\overset{O}{\|}}{C}-(CH_2)_n-\underset{}{CH}-\overset{\overset{NHX}{|}}{\underset{}{C}}-OH \qquad (VI)$$

(formula VI with NHX on the CH and O double-bonded to second C, ending in OH)

wherein n and X are as defined above, in the presence of a protease, preferably a metalloprotease, in an aqueous medium, whereby the addition compound of the formula (I) wherein $R_3$ is the same as $R_2$ and $R_4$ is the same as $R_1$, precipitates.

The addition compound of the formula (I), the amino acid ester of the formula (V) and the N-protected aminodicarboxylic acid of the formula (VI) will hereinafter be referred to simply as the addition compound, the amino acid ester, and the N-protected aminodicarboxylic acid, respectively.

The above mentioned process for the preparation of the addition compound may be conducted under the conditions as disclosed in U.S. Pat. Nos. 4,165,311 and 4,256,836. For example, the following conditions may be employed.

| | |
|---|---|
| Concentrations of the amino acid ester and the N—protected aminodicarboxylic acid in the aqueous medium | From about 0.1 to about 5 M, preferably, from about 0.2 to about 2 M |
| Molar ratio of the amino acid ester to the N—protected aminodicarboxylic acid | From about 5:1 to about 1:5, preferably from 2:1 to about 1:4 |
| Enzymes | Proteases such as acidic proteases, thiol proteases, metalloproteases and serine proteases, preferably metalloproteases such as Prolisin, Thermolysin, Tasinase and P-protease. A crude enzyme of e.g. Thermoase may also be used. |
| Enzyme concentration | Usually from about 2 to about 400 mg per mol of the substrate (i.e. from about $5 \times 10^{-5}$ to about $1 \times 10^{-2}$ m mol), preferably from about 5 to about 100 mg per mol of the substrate (i.e. from about $1 \times 10^{-4}$ to about $3 \times 10^{-3}$ m mol). |
| pH of the solution at the time of the reaction | Within a range wherein the enzyme exerts it's proteolytic activity, usually at a pH of from about 4 to about 9, preferably from 4 to 8. |
| Reaction temperature | Within a temperature range wherein the enzyme can maintain its enzymatic activity, perferably from about 20° to about 50°C. |

In this process, the amino acid ester and the N-protected aminodicarboxylic acid are used respectively in the L-form or a mixture of the L- and D-forms. When a L-amino acid ester is used, there will be obtained an addition compound of a L,L-dipeptide ester with a L-amino acid ester. When a mixture of a L-amino acid ester and a D-amino acid ester is used, an addition compound will be obtained of a L,L-dipeptide ester with a D-amino acid ester or a mixture of D- and L-amino acid esters.

The aqueous mixture of the present invention may also be prepared by reacting the amino acid ester with a dipeptide ester represented by the general formula $$HO-\overset{\overset{O}{\|}}{C}-(CH_2)_n-CH-\overset{\overset{NHX}{|}}{\underset{}{C}}\overset{\overset{O}{\|}}{}-NH-\underset{\underset{R_3}{|}}{CH}-\overset{\overset{O}{\|}}{C}-O-R_4 \qquad (VII)$$

where $R_3$, $R_4$, n and X are defined above, in an aqueous medium. The addition compound thereby obtained is useful for optical resolution of the D,L-amino acid esters as disclosed in Japanese Unexamined Patent Publication No. 19234/80 and No. 73644/80.

The aqueous mixture to be used in the present invention is not restricted to the one obtained by the above mentioned processes, and may be an aqueous suspension obtained by suspending in water an addition compound prepared by the above mentioned processes or any other processes.

When an organic solvent capable of forming a binary phase system with water is added to the thus obtained aqueous mixture thus obtained, crystals of the addition compound transfer in the solid state to the organic solvent phase, to form a slurry.

As a suitable organic solvent capable of forming a binary phase system, there may be mentioned an aromatic hydrocarbon such as benzene or toluene, an aliphatic hydrocarbon such as n-hexane, n-heptane or cyclohexane, an ether such as diethyl ether or diisopropyl ether, a ketone such as methylisobutyl ketone, dibutyl ketone or diisobutyl ketone, or a mixture thereof.

In the present invention, the organic solvent is used to separate the addition compound in a form of a slurry of the solvent, and the solvent is used in an amount allowing to remain a substantial portion of the addition compound in solid state. The amount of the organic solvent is usually from about 1 to about 20 parts by weight, preferably from about 1 to about 15 parts by weight, more preferably less than 10 parts by weight and not less than 1 part by weight, based on 1 part by weight of the addition compound.

When the binary phase system comprising an organic solvent phase and an aqueous phase is formed, so that the addition compound is suspended in the organic phase, the organic solvent contains the addition compound substantially in a solid slurry, form although a part of the addition compound will be dissolved in the organic solvent depending upon its solubility.

The amount of water in the aqueous mixture used as the starting material of the present invention is not critical, but is usually from about 0.3 to about 20 parts by weight, preferably from about 0.5 to about 15 parts by weight, based on 1 part by weight of the adidition compound.

In the present invention, the temperature at the time of contacting the aqueous mixture containing the addition compound with the organic solvent is usually from about 0° to about 80° C. However, in a case where the remaining protease is to be recovered from the aqueous phase, the mixing is preferably carried out at a temperature of from about 5° to about 50° C. The length of time for the mixing or the phase separation is not critical, and is usually from 5 minutes to 3 hours.

The organic solvent phase containing the substantial portion of the addition compound in a form of a slurry can be separated from the aqueous phase containing the protease by conventional means commonly employed in liquid-liquid separations. The majority of the amino acid ester, N-protected aminodicarboxylic acid and protease remained unreacted or not inactivated in the above mentioned reaction for the formation of the addition compound, remain in the aqueous phase. Accordingly the addition compound can thereby be separated from them. The addition compound can be isolated from the separated organic phase by conventional means such as filtration or removal of the organic solvent by evaporation.

It is also possible to contact the separated organic phase with an aqueous acidic solution so that the amino acid ester as a constituent of the addition compound is transferred to the aqueous phase, whereupon the amino acid ester is isolated from the aqueous phase while the dipeptide ester, as the other constituent of the addition compound, is isolated from the organic solvent.

After the separation of the organic solvent phase from the aqueous phase, water and a bronsted acid are added to, and mixed with, the separated organic solvent phase, and the mixture thereby obtained is subjected to phase separation to form (1) a second organic solvent phase containing a dipeptide ester derivative of the formula

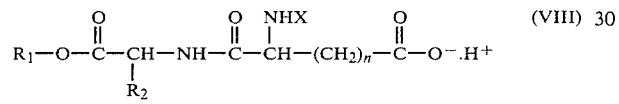

wherein $R_1$, $R_2$, X and n are as defined above, and (2) a second aqueous phase containing an amino acid ester ion of the formula

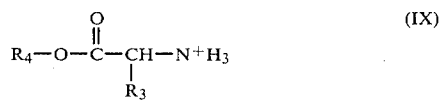

wherein $R_3$ and $R_4$ are as defined above. The two phases are there separated from each other, and the final dipeptide derivative is recovered from the second organic solvent phase, while an amino acid ester of the formula

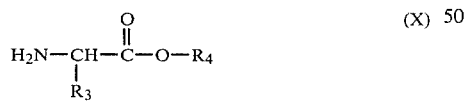

where $R_3$ and $R_4$ are as defined above, is recovered from the second aqueous phase.

In this case, if X in the dipeptide ester is a benzyloxycarbonyl group, it is particularly advantageous to use toluene as the organic solvent because toluene can readily be recovered and reused, as will be described hereinafter.

The amount of water to be added to the first organic solvent phase separated from the first aqueous phase is usually from about 0.5 to about 15 parts by weight, preferably from about 1 to about 10 parts by weight, based on 1 part by weight of the addition compound, including water derived from the acid. When the acid is used in a form of an aqueous solution, the required amount of water may be added in the form of the aqueous solution of the acid.

The acid to be added together with water for the reaction with the addition compound is an inorganic or organic bronsted acid. As the inorganic brønsted acid, there may be mentioned hydrochloric acid, hydrobromic acid, sulfuric acid or phosphoric acid. As the organic brønsted acid, there may be mentioned formic acid, acetic acid, citric acid or toluene sulfonic acid. These acids may be used in a form of an aqueous solution. The concentration of the acid in the aqueous solution is not critical and may be optionally determined in order that the amount of water falls within the above specified range.

A solid acid such as a H-type cation exchange resin may also be used. In this case, such a solid acid will settle at the bottom of the system.

The essential function of the acid is to electrolytically dissociate the amino acid ester moiety of the addition compound and thereby to form an aqueous solution of a salt of the amino acid ester. However, in the case where a solid acid is used, the amino acid ester is ion-exchanged with the hydrogen ions of the solid acid and withdrawn from the aqueous phase system. Therefore, the amount of the acid relative to the amount of the addition compound in the aqueous mixture as the starting material, is a stoichiometric amount or more, i.e. from about 1 to about 100 equivalents, preferably from about 1 to 20 equivalents, more preferably from about 1 to 10 equivalents based on 1 mol of the addition compound. However, in some cases the dipeptide ester is not required to be so pure depending upon the particular purpose. In such cases, the acid may be used in an amount of less than the stoichiometric amount.

The separation of the dipeptide after the electrolytic dissociation of the addition compound is usually carried out by transferring it to the organic solvent in a form of slurry. However, when a ketone capable of forming a binary phase system with water is used, the separation may be carried out in a form of its solution.

The temperature at the time of treating the addition compound in this embodiment, is usually from about 0° to about 100° C., preferably from about 5° to about 80° C. The dissociation reaction of the addition compound is usually completed within 10 minutes provided stirring is adequately conducted.

When the protective group X is a group which is relatively susceptible to hydrolysis, such as a p-methoxybenzyloxycarbonyl group, due care should be taken for the control of the reaction time and the reaction temperature to avoid the freeing of the group except for a case where the freeing of the group is desired or permissible.

When contacted with the acid, the solid addition compound will be dissociated into a dipeptide ester and a salt of an amino acid ester with the acid. Since the dipeptide ester has low solubility in the aqueous acidic solution, a substantial portion thereof is present in the organic solvent phase in a form of a slurry or solute. On the other hand, the salt of the amino acid ester is highly soluble in the aqueous acidic solution and dissolves in the aqueous phase. When a solid acid is used, the amino acid ester precipitates as its salt. Thus, the reaction system results in a binary phase system comprising an organic phase containing the dipeptide ester in a form of a slurry or solute and an aqueous solution of the salt of the amino acid ester. The separation of the binary phase system can be carried out by a conventional liquid-liquid separation method. The recovery of the amino acid ester from the solid acid salt can also readily be performed by a conventional method.

The dipeptide ester can be recovered from the organic slurry phase by conventional methods such as filtration, centrifugal separation or removal of the solvent by evaporation. Otherwise, the organic slurry phase may directly be subjected to the next step of the reaction for removal of the protective group. Especially in the case where X in the formula (I) for the dipeptide ester is a benzyloxycarbonyl group and the organic solvent is toluene, if water is added to the separated organic slurry phase and the removal of the benzyloxycarbonyl group is carried out reductively, the dipeptide ester with its amino group having the protective group removed transfers to the aqueous phase. It is thereby possible not only to effectively carry out the removal of the N-protective groups but also to have the protective groups once recovered converted to toluene which is the same as the solvent. Thus, the removal reaction does not lead to contamination of the solvent, and toluene used as the solvent can readily be recovered for reuse.

This method is particularly useful for industrial production of Aspartame which is a low calorie sweetener, when the addition compound has the general formula (I) wherein each of $R_1$ and $R_4$ is a methyl group, each of $R_2$ and $R_3$ is a benzyl group and n is 1.

It is possible to recover the amino acid ester from the aqueous acidic solution separated from the organic phase by conventional methods, e.g. by concentrating the acidic solution to let the amino acid ester crystallize in the form of a salt, or by alkalinizing the solution followed by extraction with a suitable organic solvent. The recovery of the amino acid ester from the salt of a solid acid can also readily be conducted by a conventional method.

When the addition compound to be used as the starting material of the present invention is prepared by the above mentioned method of U.S. Pat. Nos. 4,165,311 and 4,256,836, the dipeptide moiety thereof is in L,L-configuration, while the amino acid ester moiety thereof is in one of L-configuration, D-configuration or a mixture of D- and L-configurations. The process of the present invention is applicable to any one of these variations in the configuration. The process is likewise applicable to the case where the dipeptide moiety is in D,D-configuration, D,L-configuration or L,D-configuration.

The dipeptide ester obtained by the process of the present invention is per se useful as an intermediate for peptide synthesis, and a dipeptide ester obtainable by removing the amino protective group X therefrom is also a useful compound. For instance, an α-L-aspartyl-L-phenylalanine methyl ester is useful as a sweetener. Optically resolved amino acid esters are obtainable from the addition compound formed by mixing a dipeptide ester and racemic amino acid esters. Thus, the process is useful as a method for optical resolution.

According to a further embodiment of the present invention, an acid, preferably the above mentioned brønsted acid, is added to the starting aqueous mixture together with the organic solvent at the time of the admixing of the organic solvent with the aqueous mixture, whereby the addition compound, i.e. the dipeptide ester derivative of the above formula (I) wherein Y is an ammonium derivative ion of the above formula (II) is electrolytically dissociated by the acid into a dipeptide derivative of the above formula (III) wherein Z is a hydrogen ion and an amino acid ester of the above formula (X), and the dipeptide derivative transfers to the organic solvent phase substantially in a solid state while the amino acid ester is dissolved in the aqueous phase.

The dipeptide derivative and the amino acid ester can be recovered from the organic solvent phase and the aqueous phase, respectively, in the same manners as described above with respect to the acid treatment of the separated organic phase.

The acid to be used in this embodiment is the same inorganic or organic brønsted acid as mentioned above with respect to the acid treatment of the separated organic solvent phase. The amount of the acid is likewise usually from about 1 to about 100 equivalents, preferably from about 1 to about 20 equivalents, more preferably from about 1 to about 10 equivalents based on 1 mol of the addition compound. However, the amount may be less than the stoichiometric amount in a case where the dipeptide is not required to be highly pure.

The amount of water including water derived from the acid is usually from about 0.3 to about 20 parts by weight, preferably from 0.5 to about 15 parts by weight, more preferably from about 1 to about 10 parts by weight, based on 1 part by weight of the addition compound.

Other working conditions for the acid treatment including the separation of the organic solvent phase and aqueous acidic phase, the removal of the N-protective groups and the recovery of the desired products and solvent, are basically the same as those described above for the acid treatment of the separated organic phase.

In the aqueous phase separated from the organic solvent phase, there still remains a substantial amount of the active protease. This aqueous phase may be reused after concentrating and recovering the protease by means of e.g. an ultrafiltration. Alternatively, the protease may be separated from the aqueous phase by conventional methods such as salting out and then reused. Among these methods ultrafiltration is most advantageous for the industrial operation. The material for the ultrafiltration groups is not critical and the ultrafilter may be made of a material such as polyacrylonitrile, polyamide, polyimide, polysulfone or celluloe acetate. However, proper filter having a proper fractionation properties; depending upon the molecular weight of the used protease are preferred and a minimum adsorption of the protease, are preferred. The filter module is not critical, and any one of a hollow fiber type, a spiral type, a cylinder type or a frame and plate type may be used.

The thus concentrated protease solution may be used together with the amino acid ester and the N-protected aminodicarboylic acid remained unreacted, as the raw material for the subsequent reaction for the formation of the addition compound.

Alternatively, an aqueous solution of a salt may be added to the concentrated protease solution. Filtration is there repeated to recover the protease in a form of a solution of the salt containing the protease substantially in pure form.

The thus recovered protease or its solution may be reused for the formation of the addition compound, or it may be used for other reactions in which a protease is required.

Having thus described the invention, it should be apparent that according to the present invention, the addition compound in the aqueous mixture can effectively be separated from other components and transferred into the organic solvent in a form of a highly concentrated slurry. The addition compound is not required to be completely dissolved, but the substantial portion thereof can be extracted into the organic solvent phase in a solid state, whereby the amount of the solvent required is minimized, which is industrially advantageous. It is also possible to use an organic solvent which is more stable and physiologically safer than the solvents normally used in the extraction method wherein the addition compound is dissolved. Furthermore, it is possible to recover the protease from the aqueous phase and to reuse it, thus leading to an economical advantage.

Now, the present invention will be described in detail with reference to Examples.

EXAMPLE 1

Into a 2 liter flask, 53.45 g of N-benzyloxycarbonyl-L-aspartic acid and 107.84 g of D,L-phenylalanine methyl ester hydrochloride were introduced, and 400 ml of distilled water, 100 ml of a 5N sodium hydroxide aqueous solution, 4.8 g of crude Thermolysin (Thermoase PS-160 (trademark), manufactured by Daiwa Kasei K.K.) and 0.9 g of calcium acetate monohydrate were added thereto. The mixture was reacted at 40° C. under stirring. After 15 hours, a reaction mixture in a form of a suspension was obtained. 600 ml of toluene was added and the mixture was stirred at 40° C. for 20 minutes. Upon stopping the stirring, a toluene phase containing a solid component in a suspended state and a homogeneous transparent aqueous phase were separated. 10 minutes later, the toluene phase containing the solid component was separated from the aqueous phase, and the separated toluene phase was washed twice with 200 ml of a 0.5% calcium acetate aqueous solution and then the solid component was separated by filtration with use of a glass filter. After drying it, it was recrystallized from an ethylacetate-n-hexane solvent mixture, whereby 101.1 g (yield: 83.2%) of a 1:1 addition compound of N-benzyloxycarbonyl-α-L-aspartyl-L-phenylalanine methyl ester (hereinafter referred to as "Z-APM") and phenylalanine methyl ester mainly of a D-form (hereinafter referred to as "D-PM") was obtained. These crystals were confirmed to be a 1:1 addition compound of Z-APM and mainly D-PM by the fact that the NMR, IR, elemental analysis and optical rotation were substantially identical with the data disclosed in U.S. Pat. No. 4,165,311.

EXAMPLE 2

The reactions for the formation of the peptide and for the formation of the addition compound were carried out in the same manner as in Example 1 except that 7.2 g of crude Thermolysin and 1.3 g of calcium acetate monohydrate were used and the reaction time was 8 hours.

After completion of the reactions, the same treatment as in Example 1 was carried out except that 1 liter of methylisobutyl ketone was used instead of toluene. After the separation, the methylisobutyl ketone phase containing the solid component in a suspended state was subjected to the removal of the solvent by a rotary evaporator, and the residue was recrystallized from an ethylacetate-n-hexane solvent mixture, whereby 102.2 g (yield: 84.1%) of a 1:1 addition compound of Z-APM and D-PM was obtained.

EXAMPLE 3

The reactions for the formation of the peptide and for the formation of the addition compound were carried out in the same manner as in Example 2.

After the completion of the reactions, the same treatment as in Example 2 was carried out except that 500 ml of diisopropyl ether was used instead of methylisobutyl ketone. After the separation, the diisopropyl ether phase containing the solid component in a suspended state was subjected to the removal of the solvent by a rotary evaporator, and the residue was recrystallized from an ethylacetate-n-hexane solvent mixture, whereby 96.5 g (yield: 79.5%) of a 1:1 addition compound of Z-APM and D-PM was obtained.

EXAMPLE 4

The reactions for the formation of the peptide and for the formation of the addition compound were carried out in the same manner as in Example 2 except that L-phenylalanine methyl ester hydrochloride was used instead of D,L-phenylalanine methyl ester hydrochloride.

After completion of the reactions, the after-treatment was carried out in the same manner as in Example 2 except that a solvent mixture comprising 900 ml of methylisobutyl ketone and 100 ml of toluene was used instead of methylisobutyl ketone. After the separation from the aqueous phase, the organic phase containing the solid component in a suspended state was subjected to the removal of the solvent by a rotary evaporator, and the residue was recrystallized from an ethyl acetate-n-hexane solvent mixture, whereby 98.68 g (yield: 81.2%) of a 1:1 addition compound of Z-APM and L-phenylalanine methyl ester (hereinafter referred to as "L-PM") was obtained.

The addition compound was confirmed to be a 1:1 addition compound of Z-APM and L-PM by the fact that the NMR, IR, elemental analysis and optical rotation were identical with the data disclosed in U.S. Pat. No. 4,165,311.

EXAMPLE 5

Into a 200 ml flask, 5.345 g of N-benzyloxycarbonyl-α-L-aspartic acid and 10.784 g of D,L-phenylalanine methyl ester hydrochloride were introduced, and 40 ml of distilled water, 10 ml of a 5N sodium hydroxide aqueous solution, 200 mg of Thermolysin and 130 mg of calcium acetate monohydrate were added. The mixture was reacted at 40° C. under stirring. After 7 hours, 100 ml of methylisobutyl ketone were added to the reaction mixture, and the mixture was stirred at 40° C. for 20 minutes. Upon expiration of 10 minutes after the termination of the stirring, the organic phase containing the solid component was separated from the homogeneous aqueous phase, and the separated organic phase was washed twice with 20 ml of a 0.5% calcium acetate aqueous solution and then subjected to the removal of the solvent by a rotary evaporator, and the residue was recrystallized from ethylacetate-n-hexane, whereby 10.34 g (yield: 85.2%) of a 1:1 addition compound of Z-APM and mainly D-PM was obtained.

EXAMPLE 6

The peptide formation, the formation of the addition compound and the treatment after the reactions were carried out in the same manner as in Example 5 except that 1 g of PS-protease was used instead of Thermolysin. After the recrystallization, 9.87 g (yield: 81.2%) of a 1:1 addition compound of Z-APM and mainly D-PM was obtained.

EXAMPLE 7

In 20 ml of water, 5.0 g of a sodium salt of N-benzyloxycarbonyl-α-L-aspartyl-L-phenylalanine methyl ester was dissolved, and this solution was dropwise added to 20 ml of an aqueous solution containing 5.0 g of D,L-valine methyl ester under stirring. After leaving the mixture to stand at room temperature for 2 hours, 50 ml of methylisobutyl ketone was added and stirred. The organic solvent phase was separated from the aqueous phase, filtered and dried, whereby 5.9 g of an addition compound of N-benzyloxycarbonyl-α-L-aspartyl-L-phenylalanine methyl ester and valine methyl ester was obtained.

This addition compound was treated with a 1N hydrochloric acid aqueous solution, whereby D-valine methyl ester having an optical purity of 72% was obtained.

EXAMPLE 8

In Example 1, the separated aqueous phase and the washing solutions were combined (the total amount: 840 ml) and the enzymatic activity of the combined solution was measured by a casein digestion method, whereby the residual activity was found to be 88% of the charged protease. This aqueous solution was concentrated to 200 ml by means of a polysulfone hollow fiber type ultrafiltration apparatus (H1P5, manufactured by Amicon Co.; fractional molecular weight: 5,000; filter surface area: 0.05 m$^2$; inner diameter of the hollow fiber: 0.5 mm). The enzymatic activity of the concentrated solution was 86% of the charged protease.

With use of the protease solution thus obtained, the reaction for the formation of the addition compound was repeated (this protease solution was used for substitution of 200 ml out of 400 ml of the distilled water and the amount of crude Thermolysin added was 0.6 g). Substantially the same results as in the first formation reaction were obtained.

EXAMPLE 9

In Example 2, the separated aqueous phase and the washing solutions were combined (the total amount: 840 ml) and the enzymatic activity of the combined solution was 90% of the charged protease. This solution was concentrated to 200 ml by means of a polyacrylonitrile hollow fiber ultrafiltration apparatus (HL-100 Model, manufactured by Asahi Chemical Industries Co. Ltd.; fractional molecular weight: 6,000; filter surface area: 0.2 m$^2$; inner diameter of the hollow fiber: 0.8 mm).

The enzymatic activity of the concentrated solution was 75% of the charged protease.

EXAMPLE 10

In Example 3, the separated aqueous phase and the washing solutions were combined (the total amount: 680 ml), and the enzymatic activity of the combined solution was 72% of the charged protease.

This solution was concentrated to 200 ml by means of a polyimide cylinder type ultrafiltration apparatus (NTU-4220, manufactured by Nitto Denki Kogyo K.K.; the filter surface area: 0.014 m$^2$; fractional molecular weight: 20,000).

The enzymatic activity of the concentrated solution was 70% of the charged protease.

EXAMPLE 11

In Example 4, the separated aqueous phase and the washing solutions were combined (the total amount: 920 ml), and the enzymatic activity of the combined solution was 92% of the charged protease.

This solution was concentrated to 200 ml in the same manner as in Example 8.

The enzymatic activity of the concentrated solution was 88% of the charged protease.

Further, the filtration of the solution was conducted at a constant quantity of 200 ml while continuously adding a 0.5% calcium acetate aqueous solution thereto to supplement the amount reduced by the filtration, whereby a 0.5% calcium acetate aqueous solution of crude Thermolysin containing substantially no other components was obtained. The crude Thermolysin solution thereby obtained had an enzymatic activity of 85% of the charged protease.

EXAMPLE 12

In Example 5, the separated aqueous phase and the washing solutions were combined (the total amount: 70 ml), and the enzymatic acitivity of the combined solution was 82% of the charged protease.

This solution was concentrated to 20 ml by means of a polyacrylonitrile hollow fiber ultrafiltration apparatus (Minimodule NH-3 Model, manufactured by Asahi Chemical Industries Co., Ltd; HI filter; filter surface area: 25 cm$^2$; inner diameter of the hollow filament: 0.8 mm; fractional molecular weight: 6,000).

The enzymatic activity of the concentrated solution was 77% of the charged protease.

EXAMPLE 13

In Example 6, the separated aqueous phase and the washing solutions were combined, and the enzymatic activity of the combined solution was 84% of the charged protease.

The solution was concentrated in the same manner as in Example 12, and the enzymatic activity of the concentrated solution was 78% of the charged protease.

EXAMPLE 14

Into a 2 liter flask, 53.45 g of N-benzyloxycarbonyl-L-aspartic acid and 107.84 g of D,L-phenylalanine methyl ester hydrochloride were introduced, and 400 ml of distilled water, 100 ml of a 5N sodium hydroxide aqueous solution, 7.2 g of crude Thermolysin (Thermoase PS-160 (trademark), manufactured by Daiwa Kasei K.K.) and 1.3 g of calcium acetate monohydrate. The mixture was reacted at 40° C. under stirring. After 8 hours, the reaction mixture became an aqueous mixture containing the reaction product in a suspended state. To this aqueous mixture, 700 ml of toluene was added and stirred at 40° C. for 20 minutes. Upon stopping the stirring, a toluene phase containing a solid component in a suspended state and a homogeneous transparent aqueous phase were separated.

A part of the solid component was sampled, recrystallized from ethylacetate-n-hexane and analyzed in the same manner as in Example 1, whereby it was confirmed to be a 1:1 addition compound of Z-AMP and mainly D-PM.

The toluene phase was separated from the aqueous phase, and 500 ml of a 1N hydrochloric acid aqueous solution was added thereto. The mixture was stirred at 60° C. for one hour. After leaving the mixture to stand for about 20 minutes, the toluene phase containing the solid component was separated from the homogeneous transparent aqueous phase.

The separated toluene phase was washed twice with 200 ml of distilled water at 60° C., and cooled to room temperature. The crystals in the toluene phase were collected by filtration under reduced pressure by means of a glass filter and dried, whereby 73.42 of Z-APM was obtained (overall yield relative to the starting material: 85.2%; purity: 99.4%).

EXAMPLE 15

Into a 2 liter flask, 53.45 g of N-benzyloxycarbonyl-L-aspartic acid and 86.27 g of L-phenylalanine methyl ester hydrochloride were introduced, and 350 ml of distilled water, 90 ml of a 5N sodium hydroxide aqueous solution, 4.8 g of crude Thermolysin (Thermoase PS-160 (trademark), manufactured by Daiwa Kasei K.K.) and 0.9 g of calcium acetate monohydrate were added. The mixture was reacted at 40° C. under stirring. After 5 hours, 600 ml of toluene was added to the reaction mixture, and the mixture was stirred at 40° C. for 20 minutes. Upon stopping the stirring, a toluene phase containing a solid component in a suspended state and a homogeneous transparent aqueous phase were separated.

A part of the solid component was sampled, recrystallized from ethylacetate-n-hexane and analyzed in the same manner as in Example 1, whereby it was confirmed to be a 1:1 addition compound of Z-APM and L-PM.

The toluene phase was separated from the aqueous phase, and 500 ml of a 1N hydrochloric acid aqueous solution was added. The mixture was stirred at 60° C. for one hour. After leaving the mixture to stand still for 20 minutes, the toluene phase containing the solid component was separated from the homogeneous transparent aqueous phase. After cooling the separated toluene phase, the crystals contained therein were collected by filtration under reduced pressure by means of a glass filter and dried, whereby 73.27 g of Z-APM was obtained (overall yield relative to the starting material: 85.3%; purity: 99.7%).

EXAMPLE 16

To a suspension prepared by suspending 4.25 g of a 1:1 addition compound of Z-APM and D-PM in 35 ml of toluene, 10 ml of a 1N hydrochloric acid and 20 ml of distilled water were added. The mixture was stirred at 60° C. for 30 minutes. After leaving the mixture to stand still for 20 minutes, the toluene phase containing the solid component was separated from the homogeneous transparent aqueous phase. The toluene phase was washed twice with 20 ml of distilled water and subjected to the removal of the solvent by evaporation by means of a rotary evaporator, whereby 2.92 g of Z-APM (purity: 99.7%) was obtained.

EXAMPLE 17

The operation was performed in the same manner as in Example 16 except that diisopropyl ether was used instead of toluene. The solvent was removed from isopropyl ether phase containing the solid component by evapolation by means of a rotary evaporator, whereby 2.96 g of Z-APM (purity: 98.0%) was obtained.

EXAMPLE 18

The operation was performed in the same manner as in Example 16 except that the temperature and time for the admixing the toluene suspension of the addition compound and the hydrochloric acid aqueous solution were changed to 25° C. and 60 minutes, respectively, whereby 2.96 g of Z-APM (purity: 98.1%) was obtained.

EXAMPLE 19

The operation was performed in the same manner as in Example 16 except that 0.715 ml of a 95% sulfuric acid was used instead of hydrochloric acid and 26.3 ml of distilled water was used instead of 20 ml of the same, whereby 2.96 g of Z-APM (purity: 99.6%) was obtained.

EXAMPLE 20

The operation was performed in the same manner as in Example 19 except that 0.733 ml of acetic acid was used instead of the 95% sulfuric acid, whereby 3.06 g of Z-APM (purity: 91.7%) was obtained.

EXAMPLE 21

The operation was performed in the same manner as in Example 16 except that n-heptane was used instead of toluene, whereby 3.12 g of Z-APM (purity: 89.6%) was obtained.

EXAMPLE 22

In 20 ml of water, 5.0 g of a sodium salt of N-benzyloxycarbonyl-α-L-aspartyl-L-phenylalanine methyl ester was dissolved, and this solution was dropwise added to 20 ml of an aqueous solution containing 5.0 g of D,L-valine methyl ester hydrochloride under stirring, whereupon the reaction product precipitated and the reaction mixture became a suspension. After leaving this suspension to stand at room temperature for 2 hours, 50 ml of methylisobutyl ketone was added thereto, stirred and then left to stand still, whereupon a methylisobutyl ketone suspension phase containing the reaction product and a homogeneous transparent aqueous phase were separated. The methylisobutyl ketone suspension phase was separated from the aqueous phase, and 10 ml of a 1N hydrochloric acid aqueous solution and 20 ml of water were added thereto. The mixture was stirred at 60° C. for 30 minutes and then left to stand still, whereupon a homogeneous methylisobutyl ketone phase and a homogeneous aqueous phase were separated.

Methylisobutyl ketone was removed from the methylisobutyl ketone phase by evaporation by means of a rotary evaporator, whereby 4.5 g of Z-APM (purity: 99.5%) was obtained.

On the other hand, the aqueous phase was brought to pH 8 with an addition of sodium carbonate, and then extracted with dichloromethane. The dichloromethane phase was dried over anhydrous magnesium sulfate, and after blowing hydrogen chloride gas into it, it was concentrated. Diethyl ether was further added thereto to let crystals precipitate, and the crystals were collected. 1.6 g of crystals of D-valine methyl ester hydrochloride (optical purity: 69%) were obtained.

EXAMPLES 23 TO 26

The operations were performed in the same manner as in Example 16 except that instead of the 1:1 addition compound of Z-APM and D-PM, 5.00 g of 1:1 addition compounds of Z-APM and amino acid esters other than phenylalanine methyl ester were used. The results thereby obtained are shown below:

| Examples | Addition Compounds | Recovered Z-APM (purity) |
|---|---|---|
| 23 | D-valine methyl ester | 3.76 g (98.3%) |
| 24 | L-alanine ethyl ester | 3.82 g (99.4%) |
| 25 | D-leucine methyl ester | 3.71 g (99.1%) |
| 26 | L-tyrosine ethyl ester | 3.11 g (98.4%) |

EXAMPLE 27

The operation was performed in the same manner as in Example 16 except that instead of the 1:1 addition compound of Z-APM and D-PM, 5.00 g of a 1:1 addition compound of N-benzyloxycarbonyl-$\alpha$-L-aspartyl-L-phenylalanine ethyl ester (Z-APE) and D-PM was used, whereby 3.42 g of Z-APE (purity: 98.8%) was obtained.

EXAMPLE 28

The operation was performed in the same manner as in Example 16 except that instead of the 1:1 addition compound of Z-APM and D-PM, 5.00 g of a 1:1 addition compound of N-p-methoxybenzyloxycarbonyl-$\alpha$-L-aspartyl-L-phenylalanine methyl ester (PMZ-APM) and D-PM was used and the contacting temperature of the toluene suspension with the aqueous hydrochloric acid solution was 20° C., whereby 3.45 g of PMZ-APM (purity: 97.2%) was obtained.

EXAMPLE 29

Into a 2 liter flask, 53.45 g of N-benzyloxycarbonyl-L-aspartic acid and 107.84 g of D,L-phenylalanine methyl ester hydrochloride were introduced, and 400 ml of distilled water, 100 ml of a 5N sodium hydroxide aqueous solution, 7.2 g of crude Thermolysin (Thermoase PS-160 (trademark), manufactured by Daiwa Kasei K.K.) and 1.3 g of calcium acetate monohydrate were added thereto. The mixture was reacted at 40° C. under stirring. After 8 hours, a part of a solid component in the aqueous mixture in a form of a suspension was sampled, thoroughly washed with cold water, dried and analyzed in the same manner as in Example 1, whereby the solid component was confirmed to be a 1:1 addition compound of Z-APM and mainly D-PM.

To the aqueous mixture i.e. the reaction mixture, 600 ml of toluene and 100 ml of concentrated hydrochloric acid were added and the mixture was stirred at 60° C. for one hour and then left to stand still for about 20 minutes, whereupon the toluene phase containing a solid component was separated from the homogeneous transparent aqueous phase. The separated toluene phase was washed twice with 200 ml of distilled water at 60° C., and then cooled to room temperature, and crystals in the toluene phase were collected by filtration under reduced pressure by means of a glass filter, and dried, whereby 74.45 g of Z-APM was obtained (overall yield relative to the starting material: 86.3%; purity: 99.3%).

EXAMPLE 30

The reaction was conducted in the same manner as in Example 29 except that L-phenylalanine methyl ester hydrochloride was used instead of D,L-phenylalanine methyl ester hydrochloride, 3.6 g of crude Thermolysin was used instead of 7.2 g of the same, and 0.6 g of calcium acetate monohydrate was used instead of 1.3 g of the same. After 8 hours, a part of a solid component was sampled from the aqueous mixture in a form of a suspension, thoroughly washed with cold water, dried and then analyzed in the same manner as in Example 1, whereby the solid component was confirmed to be a 1:1 addition compound of Z-APM and L-PM.

The aqueous mixture i.e. the reaction mixture was treated in the same manner as in Example 29 and Z-APM was obtained by filtration of the toluene phase in an amount of 74.56 g as dried (overall yield relative to the starting material: 86.4%; purity: 99.3%).

EXAMPLE 31

In a suspension obtained by suspending 5.00 g of a 1:1 addition compound of Z-APM and D-PM in 20 ml of distilled water, 35 ml of toluene and 10 ml of a 1N hydrochloric acid aqueous solution were added, and the mixture was stirred at 60° C. for 30 minutes, and then left to stand still for about 20 minutes, whereupon the toluene phase containing a solid component was separated from the homogeneous transparent aqueous phase. The separated toluene phase was washed twice with 20 ml of distilled water and subjected to the removal of the solvent by evaporation by means of a rotary evaporator, whereby 3.49 g of Z-APM (purity: 99.5%) was obtained.

EXAMPLE 32

The operation was performed in the same manner as in Example 31 except that diisopropyl ether was used instead of toluene, whereby 3.36 g of Z-APM (purity: 97.4%) was obtained.

EXAMPLE 33

The operation was performed in the same manner as in Example 31 except that the temperature and time for mixing the aqueous suspension of the addition compound with toluene and the aqueous hydrochloric acid solution were changed to 25° C. and 60 minutes, respectively, whereby 3.45 g of Z-APM (purity: 99.7%) was obtained.

EXAMPLE 34

The operation was performed in the same manner as in Example 31 except that 10 ml of 95% sulfuric acid was used instead of hydrochloric acid and 30 ml of distilled water was used instead of 20 ml of the same, whereby 3.42 g of Z-APM (purity: 99.5%) was obtained.

EXAMPLE 35

The operation was performed in the same manner as in Example 34 except that 1.0 ml of acetic acid was used instead of 95% sulfuric acid, whereby 3.21 g of Z-APM (purity: 91.8%) was obtained.

EXAMPLE 36

The operation was performed in the same manner as in Example 31 except that n-heptane was used instead of toluene, whereby 3.21 g of Z-APM (purity: 91.8%) was obtained.

EXAMPLE 37

The operation was performed in the same manner as in Example 31 except that 5.00 g of a 1:1 addition compound of N-benzyloxycarbonyl-$\alpha$-L-aspartyl-L-phenylalanine ethyl ester (Z-APE) and D-PM was used instead of the 1:1 addition compound of Z-APM and D-PM, whereby 3.38 g of Z-APE (purity: 99.1%) was obtained.

EXAMPLE 38

The operation was performed in the same manner as in Example 31 except that a suspension of 5.00 g of a 1:1 addition compound of N-p-methoxybenzyloxycarbonyl-α-L-aspartyl-L-phenylalanine methyl ester (PMZ-APM) and D-PM was used instead of the suspension of the 1:1 addition compound of Z-APM and D-PM, and the contacting temperature of the aqueous suspension with toluene and the aqueous hydrochloric acid was 20° C., whereby 3.41 g of PMZ-APM (purity: 98.4%) was obtained.

EXAMPLE 39

80 ml of a hot ethylacetate solution containing 6.66 g of D,L-phenylalanine methyl ester and 200 ml of a hot ethylacetate solution containing 7.72 g of an N-benzyloxycarbonyl-α-L-aspartyl-L-phenylalanine methyl ester were mixed, and the mixture was left to stand at room temperature overnight, whereupon an addition compound formed was separated by filtration and dried. 5.00 g of the addition compound thus obtained was suspended in 20 ml of distilled water to obtain an aqueous mixture. To this aqueous mixture, 35 ml of toluene and 10 ml of a 1N hydrochloric acid aqueous solution were added, and the mixture was stirred at 60° C. for 30 minutes and then left to stand still for 20 minutes. The toluene phase containing a solid component was separated from the homogeneous transparent aqueous phase. The separated toluene phase was washed twice with 20 ml of distilled water and then subjected to the removal of solvent by evaporation by means of a rotary evaporator, whereby 3.47 g of Z-APM (purity: 99.6%) was obtained.

On the other hand, the aqueous phase separated from the toluene phase and the washing solutions from the washing of the toluene phase were combined, and sodium carbonate was added thereto to adjust the pH of the combined solution to 8. The solution was then extracted with dichloromethane. The dichloromethane phase was dried over anhydrous magnesium sulfate, and after blowing a hydrogen chloride gas into it, it was concentrated. Diethyl ether was further added thereto to let crystals precipitate, and the crystals were collected by filtration. 1.58 g of crystals of D-phenylalanine methyl ester hydrochloride (optical purity: 97%) were obtained.

EXAMPLES 40 TO 43

The operations were performed in the same manner as in Example 31 except that instead of the 1:1 addition compound of Z-APM and D-PM, 5.00 g of 1:1 addition compounds of Z-APM and amino acid esters other than phenylalanine methyl ester were used. The results thereby obtained are shown below:

| Examples | Addition Compounds | Recovered Z-APM (purity) |
|---|---|---|
| 40 | L-valine ethyl ester | 3.58 g (99.2%) |
| 41 | L-alanine methyl ester | 3.92 g (99.3%) |
| 42 | L-leucine ethyl ester | 3.41 g (99.1%) |
| 43 | D-tyrosine methyl ester | 3.13 g (98.8%) |

We claim:
1. A process for recovering a dipeptide comprising:
(a) admixing an aqueous mixture of a solid L-L, L-D or D-L dipeptide of the formula:

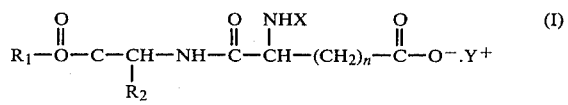

wherein
$R_1$ is a lower alkyl group;
$R_2$ is a side chain group of an amino acid selected from the group consisting of lower alkyl group and a benzyl group which may be further substituted with hydroxyl;
n is 1 or 2;
X is a benzyloxycarbonyl group which can have a nuclear substituent and
Y is a hydrogen ion, or an ammonium derivative ion of the formula

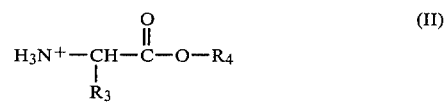

wherein
$R_3$ is a side chain group of an amino acid selected from the group consisting of lower alkyl group and a benzyl group which may be further substituted with hydroxyl; and
$R_4$ is a lower alkyl group; with an organic solvent capable of forming a binary phase system with water; said solvent being present in an amount effective to obtain the transfer of said peptide in the form of a solid from the aqueous phase to the organic solvent phase;
(b) allowing for the transfer from said aqueous phase to said solvent phase of a substantial amount of said solid dipeptide of the formula:

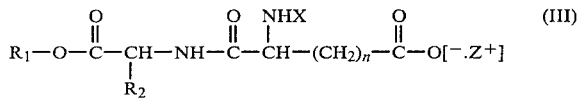

wherein $R_1$, $R_2$, n and X are as previously defined, and Z is Y,
(c) separating said solvent phase containing said solid dipeptide from said aqueous phase; and
(d) recovering said peptide from said solvent phase.
2. The process according to claim 1, wherein the moiety

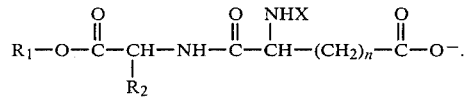

in the formulas (I) and (III) is in the L,L-configuration.
3. The process according to claim 2, wherein Y and Z are both the ammonium derivative ion of the formula

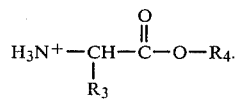

4. The process according to claim 3, wherein the organic solvent is a ketone which is capable of forming a binary phase system with water, an aliphatic or aromatic hydrocarbon, or an ether.

5. The process according to claim 4, wherein the organic solvent is used in an amount less than 10 parts and not less than 1 part, respectively by weight based on the dipeptide ester derivative.

6. The process according to claim 5, wherein $R_1$ and $R_4$ are methyl groups, $R_2$ and $R_3$ are benzyl groups, n is 1, X is a benzyloxycarbonyl group, and Y and Z are in L-, L- and D-, or D-configuration.

7. The process according to claim 5, wherein the organic solvent is toluene, methyl isobutyl ketone or isopropyl ether.

8. The process according to claim 5, wherein the aqueous mixture further contains a protease; said process further comprising a step consisting of, recovering the protease from the aqueous phase after the phase-separation of step (c).

9. The process according to claim 8, wherein $R_1$ and $R_4$ are methyl groups, $R_2$ and $R_3$ are benzyl groups, n is 1, X is a benzyloxycarbonyl group, and Y and Z are in L-, L- and D-, or D-configuration.

10. The process according to claim 9, wherein the organic solvent is toluene, methyl isobutyl ketone or isopropyl ether.

11. The process according to claim 8, further comprising after the phase separation of step (c) a step wherein, the aqueous phase is subjected to a ultrafiltration to obtain a concentrated protease solution prior to recovering the same.

12. The process according to claim 11, which further comprises prior to step (a)
reacting an amino acid ester of the formula

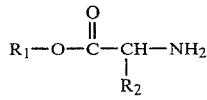

wherein
$R_1$ is a lower alkyl group and
$R_2$ is a side chain group of an amino acid selected from the group consisting of a lower alkyl group and a benzyl group; the amino acid ester being at least partially in the L-configuration, with an N-protected L-aminodicarboxylic acid of the formula

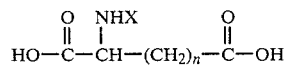

wherein
X is a benzyloxycarbonyl group which can further have a nuclear substituent, and
n is 1 or 2, in the presence of a protease in an aqueous medium at a pH effective for the protease to exert its enzymatic activity, to produce an aqueous mixture containing
(1) a dipeptide ester derivative of the formula

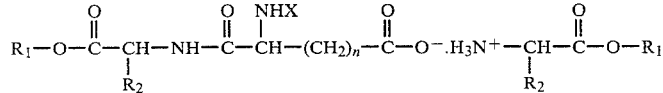

wherein
$R_1$ is a lower alkyl group, $R_2$ is a side chain group of an amino acid selected from the group consisting of a lower alkyl group and a benzyl group,
$R_3$ is $R_2$ and $R_4$ is $R_1$,
X is a benzyloxycarbonyl group which can further have a nuclear substituent, and
n is 1 or 2, the dipeptide ester derivative being in a solid state, and
(2) the protease.

13. The process according to claim 12, wherein the organic solvent is a ketone which is capable of forming a binary system with water, an aliphatic or aromatic hydrocarbon, or an ether.

14. The process according to claim 13, wherein the organic solvent is used in an amount less than 10 parts and not less than 1 part, respectively by weight based on the amount of the dipeptide ester derivative.

15. The process according to claim 14, wherein $R_1$ is a methyl group, $R_2$ is a benzyl group, n is 1, X is a benzyloxycarbonyl group, the amino acid ester is an L- or L- and D-configuration, and the moiety

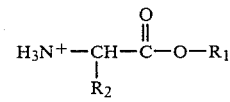

of the dipeptide ester derivative is in L-, L- and D-, or D-configuration.

16. The process according to claim 2, wherein Y and Z are both hydrogen ions.

17. The process according to claim 16, wherein the organic solvent is a ketone capable of forming a binary phase system with water, an aliphatic or aromatic hydrocarbon, or an ether, said solvent being used in an amount less than 10 parts and not less than 1 part, respectively by weight based on the amount of the dipeptide ester derivative.

18. The process according to claim 17, wherein $R_1$ is a methyl group, $R_2$ is a benzyl group, n is 1, X is a benzyloxycarbonyl group.

19. The process according to claim 2, wherein Y is the ammonium derivative ion of the formula (II) and Z is a hydrogen ion, wherein step (a) further comprises adding a bronsted acid to the aqueous mixture while admixing the organic solvent.

20. The process according to claim 19, wherein the organic solvent is a ketone capable of forming a binary phase system with water, an aliphatic or aromatic hydrocarbon, or an ether, which solvent is used in an amount less than 10 parts and less than 1 part, respectively by weight based on the amount of the dipeptide ester derivative.

21. The process according to claim 20, wherein the bronsted acid is used in an amount ranging from about 1 to about 10 equivalents based on the molarity of the dipeptide ester derivative.

22. The process according to claim 21, wherein water in the aqueous mixture is in an amount ranging from about 1 to about 10 parts by weight based on the amount of the dipeptide ester derivative.

23. The process according to claim 22, wherein hydrochloric acid, sulfuric acid or acetic acid is used as the bronsted acid.

24. The process according to claim 23, wherein $R_1$ and $R_4$ are methyl groups, $R_2$ and $R_3$ are benzyl groups, n is 1, X is a benzyloxycarbonyl group, and Z is the ammonium derivative ion of the formula (IV) which is in L-, L- and D-, or D-configuration.

25. The process according to claim 24, which further comprises after the phase-separation of step (c), recovering from the aqueous phase an amino acid ester of the formula

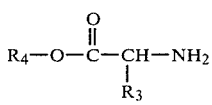

wherein $R_4$ is a methyl group and $R_3$ is a benzyl group.

26. The process according to claim 3, which further comprises, after the separation of the organic solvent phase from the aqueous phase in step (c), (e) admixing a further amount of water and a bronsted acid to the separated organic solvent phase, and (f) subjecting the mixture to phase separation to form (1) a second organic solvent phase containing a dipeptide ester derivative of the formula

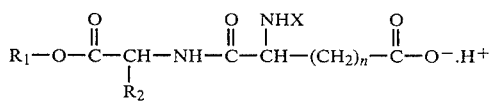

wherein $R_1$ is a lower alkyl group, $R_2$ is a side chain group of an amino acid selected from the group consisting of a lower alkyl group and a benzyl group, n is 1 or 2, X is a benzyloxycarbonyl group which can further have a nuclear substituent, and (2) a second aqueous phase containing an amino acid ester ion of the formula

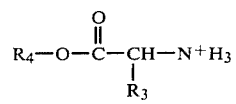

wherein $R_4$ is a lower alkyl group and $R_3$ is a side chain group of an amino acid selected from the group consisting of a lower alkyl group and a benzyl group; and (g) recovering the final dipeptide derivative from the second organic solvent phase.

27. The process according to claim 26, wherein the organic solvent is a ketone which can form a binary phase system with water, an aliphatic or aromatic hydrocarbon, an ether or a mixture thereof, said solvent being used in an amount less than 10 parts and not less than 1 part respectively, based on the amount of the dipeptide ester derivative.

28. The process according to claim 27, wherein the amount of water in the aqueous mixture ranges from about 1 to about 10 parts by weight based on the amount of the dipeptide ester derivative.

29. The process according to claim 28 wherein the bronsted acid is used in an amount ranging from about 1 to about 10 equivalents based on the molarity of the dipeptide ester derivative.

30. The process according to claim 29, wherein the water which is added with the bronsted acid to the first organic solvent phase, is in an amount ranging from about 1 to about 10 parts by weight based on the amount of the dipeptide derivative.

31. The process according to claim 30, wherein $R_1$ and $R_4$ are methyl groups, $R_2$ is a benzyl group, $R_3$ is a methyl, isopropyl, isobutyl, benzyl or p-hydroxybenzyl group, X is a benzyloxycarbonyl group or a p-methoxybenzyloxycarbonyl group and n is 1.

32. The process according to claim 31, wherein the organic solvent is toluene, methyl isobutyl ketone or diisopropyl ether, and the bronsted acid is hydrochloric acid, sulfuric acid or acetic acid.

33. The process according to claim 32, which further comprises recovering an amino acid ester of the formula

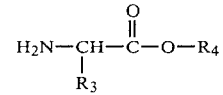

wherein $R_3$ is a benzyl group and $R_4$ is a methyl group, from the second aqueous phase.

34. The process according to claim 8, 11 or 12 wherein the protease is a metalloprotease.

* * * * *